(12) United States Patent
Luttrell

(10) Patent No.: US 7,299,192 B2
(45) Date of Patent: Nov. 20, 2007

(54) PROCESS, SYSTEM, AND COMPUTER EXECUTABLE PROGRAM ON A STORAGE MEDIUM FOR RECORDING PATIENT TREATMENT BY PROGRESS TOWARD IDENTIFIED GOALS

(76) Inventor: Tammy C. Luttrell, 1215 E. County Rd. 58, Fort Collins, CO (US) 80524

( * ) Notice: Subject to any disclaimer, the term of this patent is extended or adjusted under 35 U.S.C. 154(b) by 987 days.

(21) Appl. No.: 10/086,779

(22) Filed: Feb. 28, 2002

(65) Prior Publication Data

US 2003/0004758 A1 Jan. 2, 2003

Related U.S. Application Data

(60) Provisional application No. 60/272,075, filed on Feb. 28, 2001.

(51) Int. Cl.
*A61B 5/00* (2006.01)
(52) U.S. Cl. .......................... 705/3; 600/300
(58) Field of Classification Search ............... 705/2–3; 600/300
See application file for complete search history.

(56) References Cited

U.S. PATENT DOCUMENTS 5,016,172 A * 5/1991 Dessertine ................. 600/300
5,960,403 A * 9/1999 Brown .......................... 705/2
6,161,095 A * 12/2000 Brown .......................... 705/2
2002/0082865 A1* 6/2002 Bianco et al. ................. 705/2

OTHER PUBLICATIONS

*Coding and Payment Guide for the Physical Therapist*, American Physical Therapy Association, Dec. 1999, Table of Contents pp. i-iv and Glossary p. 403.

* cited by examiner

*Primary Examiner*—C. Luke Gilligan
*Assistant Examiner*—Russell Shay Glass
(74) *Attorney, Agent, or Firm*—Santangelo Law Offices, P.C.

(57) ABSTRACT

A process for tracking skilled-service rendered a patient by a provider at a treatment location including: generating, at the treatment location, at least one record of progress made toward each treatment goal identified for the patient and addressed by the provider during a session; receiving an input comprising each record of progress so generated, for storage as treatment record data at a host location. Data is stored in searchable data fields for access and retrieval upon command. Using the treatment record data and a host processor, a patient report is automatically generated for submitting to an entity selected from the group consisting of a health care facility, a health care provider, an insurer, the patient, an entity authorized to receive records of the patient, and a record-keeping entity for the provider. Each treatment goal identified is preferably based upon an evaluation of the patient's condition. The evaluation may take place prior to, or during, the current treatment session, by the same or another provider. A system and computer executable program code are also included.

23 Claims, 12 Drawing Sheets

Administrative Information Display — 20C

Front Range Open Gait, P.C.

Goals and Treatments
- Add/Edit Patient
- Add/Edit Doctor
- Add/Edit Therapist
- Add/Edit Insurance Company
- Updates from Medisoft
- Practice Information
- Evaluation Administration
- Main Switchboard

FIG. 2C

Evaluation/Administration Display — 20D

Front Range Open Gait, P.C.

Goals and Treatments
- Add/Edit Evaluations
- Add/Edit Categories
- Add/Edit Tools
- Add/Edit Tests
- Main Switchboard

FIG. 2D

25A  Date Entry Initials: _____

| Speech Pathology | | Physical Therapy | | Occupational Therapy | |
|---|---|---|---|---|---|
| *Evaluation Codes by Discipline* | | | | | |
| Speech Evaluation | 92506 | Physical Therapy Eval. | 97001 | Occupational Therapy Eval. | 97003 |
| | | | | | |
| | | | | | |
| Therapy Session | | | | Functional Codes | |
| Speech Treatment | 92507 | | | Direct Therapeutic Activities | 97503 |
| | | *Modalities* | | | |
| G Codes - by report | | Traction | 97012 | *Exercise* | |
| | | Electrical Stimulation | 97014 | Aquatic Therapy | 97113 |
| Speech Group Therapy | 92508 | | | | |
| MODIFIERS | | | | | |
| Distinct Procedural Service | 77mcd/59 | *Functional Codes* | | Missed Appointments | |
| | | Aquatic Therapy | 97113 | Cancelled by Therapist | 1000 |
| EPSDT CLINIC ONLY | | *Exercise* | | Cancelled by Patient | 1100 |
| Physical Test & Measurement | 97750 | Massage | 97124 | NO SHOW | 1110 |
| | | | | | |
| Office Procedures | | *Gait/Lower Quarter* | | | |
| Office Visit | 99211 | Gait Training | 97116 | | |
| Consultation | 99241 | | | | |
| Miscellaneous Codes | | | | | |
| Unlisted Procedure | 99070 | | | | |
| | | *Equipment/Community Codes* | | | |
| Location Check Box | | ADL Self Care Management | 97535 | | |
| CLINIC | | | | | |
| CLIMBING WALL | | | | Signature: | |
| HOME | | | | Witness | |
| | | ICDM 9 Codes: | | | |
| | | | | Time In:  Time Out: | |
| | | | | | |
| OTHER | | Therapist Signature: | | License # | |

FIG. 2E

Comments: — 26L ← 25B

| Goals Addressed during Treatment Session | Appropriate CPT Descriptor | Skilled Intervention Used to Address Goals: | Progress Toward Goal During/After Treatment: |
|---|---|---|---|
| | Speech Therapy | 28A | 29A |
| | Re-Evaluation/ Consultation | | |
| | Cognitive Skill | | |
| | Sensory Integration | 28B | 29B |
| | Direct Activity | | |
| | Aquatic Therapy | | |
| | Community Rehab | 28C | 29C |
| | Swallowing Treatment | | |
| | Gait Training | | |
| | Orthotics/Splinting | | |
| | Wheelchair/ Equipment | | |
| | Assistive Technology | | |
| | Manual Ther - P.T. | | |
| | Theraputic Exercise | | |

Teaching Response:

Change in Plan:      56CH

Therapist Signature:
License #:
Date Transcribed:       Initials:

☐ All records

Treatments

32A — Treatment Date [27-Dec]    33A — Session Length [15]

34A — Patient [        ]    35A — Therapist [        ]

Goal

36A

Progress

38A

31B

☐ All records

Treatments

32B — Treatment Date [11-Sep]    33B — Session Length [15]

34B — Patient [        ]    35B — Therapist [        ]

Goal

36B

Progress

PROCESS, SYSTEM, AND COMPUTER EXECUTABLE PROGRAM ON A STORAGE MEDIUM FOR RECORDING PATIENT TREATMENT BY PROGRESS TOWARD IDENTIFIED GOALS

BACKGROUND OF THE INVENTION

This application claims priority to now abandoned U.S. provisional patent application Ser. No. 60/272,075 "Method and System for Documenting Patient Treatment & Evaluation by Goal or Outcome/Progress" filed by the applicant on Feb. 28, 2001.

FIELD OF THE INVENTION

In general, the present invention relates to conventions for documenting patient evaluation, treatment, and progress (including follow-up) for purposes of creating and maintaining a patient record thereof and seeking payment or reimbursement from a medical insurance carrier, government-backed payor, contracting health maintenance or managed-care organization, or other payor. More particularly, the invention is directed to a novel automated documentation technique and associated computerized system for tracking, on a regular basis, by recording patient treatment rendered by therapists, as well as any ancillary and primary health professional/provider rendering skilled services to a human or veterinary patient.

Once an evaluation, or re-evaluation (in the event the patient has been evaluated earlier), of a condition/impairment of a patient at a treatment session (or office visit) is done by a provider, a functional "goal" is identified (if not already done so) against which progress is measured during that treatment session and any following sessions held based upon a "plan", or prescription for follow-up treatment or remedy. Patient progress toward each identified functional goal during a particular treatment session is documented (either manually or entered via user interface such as a monitor screen or other information display) and a treatment record is generated and stored therfor. Treatment record data, comprising treatment records of the patient's progress during a treatment session, are retrieved and used to automatically generate a variety of reports in a systematic manner for submission in connection with a range of purposes such as to seek reimbursement from, or report patient progress to, any one or more of the following: a physician, dentist, or other primary or ancillary health care provider caring for the patient; a hospital, out-patient clinic, laboratory/testing center, nursing home, or any other health care facility; a health maintenance organization (HMO), physician managed group (PMG), preferred provider organization (PPO) under an auto insurance plan, point of service (POS) group, or any other managed care organization; a private medical insurance carrier; government-sponsored or supported insurance such as Medicaid and Medicare; the patient, his/her legal guardian, or other person with authorization to obtain the patient's records; an entity that maintain records for the provider; and so on. Confidential reports can be generated as contemplated according to the invention, these include reports containing, by way of example only: goals identified over a select time period, e.g., monthly, weekly, daily, or per-session, for a particular patient; progress made over a selected time period, e.g., semiannually, monthly, or biweekly, weekly, daily or per-session, toward meeting active goals for a patient; comprehensive evaluation for submission to a health care provider or facility (clinic, hospital, etc.); treatment plan or prescription summary for a patient; summary of all active and completed goals for all current and discharged patients, or a select subset thereof, of the provider treated over a select time period, e.g., monthly or semiannually; as well as other reports tailored (e.g., patient- or provider-specific) to include information from the searchable display fields into which data has been entered and stored.

The technique of the invention focuses on continuity of care and treatment of human and veterinary patients across a wide variety of therapy and health care disciplines providing a systematic, yet flexible, format for:

(a) patient evaluation and associated goal-setting connected with treatment rendered to patients for whom a diagnosis has been made (diagnosis, as used throughout, to include identification of any condition/impairment of the patient);

(b) concise record-keeping and tracking of each patient's progress/outcome resulting from treatment rendered based upon each functional goal (for which results are preferably measurable) identified during a prior or current treatment session/visit;

(c) more-consistent care of patients across providers and from treatment session-to-session due to a focus on treatment goals identified based upon an evaluation of the patient's current condition as well as the access to information from treatment, plan, and evaluation record data maintained about each patient; and (d) more-consistent and comprehensive reporting to an insurer (whether it be a health care provider or facility under a managed care plan, a managed care organization, private carrier, government-sponsored carrier, etc.) or the patient, in an efficient manner, for timely payment to the provider for the skilled-services rendered.

One widely used manual method of recording/documenting clinical treatment rendered a patient employed as a standard in the physical, occupational, and speech therapy disciplines is known by the acronym SOAP (Subjective Objective Assessment Plan)—wherein a treatment is rendered to a patient based upon a diagnosis made and records are hand-written stating which later-identified goal was addressed. The *Coding and Payment Guide for the Physical Therapist* (2000 edition) sets forth procedures for implementing and carrying out SOAP. Application of appropriate skilled-intervention and the collection of relevant information about progress made during an office visit is paramount to meeting a health care professional's duty as it relates to acceptable, applicable standard(s) of care. Therefore, a streamlined process for acquisition of pertinent data specific to the patient, including any evaluation or re-evaluation of the patient's condition performed, as well as a more-efficient mechanism of reporting progress made during treatment visits, was needed.

Unlike known manual, labor intensive methods used to document clinical treatment of patients, the automated novel technique and system for tracking, on a regular basis, patient treatment as more-fully described herein, including the several additional pages labeled ATTACHMENT A depicting information displays and samples of associated miscellaneous reports/documents/summaries (all of which is fully-incorporated herein by reference), allow for continuity of care and reporting for purposes of tracking patient progress and eventual submission for payment to the provider of treatment rendered. The focus of the invention is on efficient data organization and documentation for later use, of the information collected and input concerning the skilled intervention employed to address identified goals for the patient as well as the outcome/progress made during a treatment session.

The system of the invention preferably incorporates a computerized apparatus (whether of a large or small footprint, desktop, floor, or room model, etc.) which has been programmed to communicate with at least one remote processor interconnected with at least one network, including a LAN (local area network), a privately accessible WAN (wide area network), the publically accessible WAN known as the Internet global information network, or any suitable interconnected system of processors for carrying out the automation features. One will appreciate the invention further includes a novel computer executable program code on a computer readable storage medium for tracking skilled-service rendered a patient by a provider at a treatment location.

GENERAL TECHNICAL BACKGROUND DISCUSSION

I. The Internet and Digital Computers

The Internet is a massive world-wide "network of networks" comprised of tens-of-thousands of smaller regional networks, that interconnects computerized devices of many various types and sizes (palmtop/handhelds, notebook-sized, desktops, cellular-modem message/pager devices, workstation, mainframes, etc.) allowing users of the computerized devices access to information stored around the world. Although other types of computers are undergoing development, such as computers using biological processors, digital computers (including personal computers, PCs, of any make or model) are by far the most common type currently used. The software applications that run on a digital computer are controlled by an operating system (OS). An OS performs various operations including: job management (coordinating the running of programs); provides the interaction between a user and the OS; device management (translating data to and from different input and output devices); data management (regulating data storage in memory and other storage media); task management (allocating tasks, especially in multitasking computers, for concurrent operation of one or more jobs/programs); and system security (precluding unauthorized users from access to the OS). One type of OS, for example, the powerful UNIX workstation operating system allows many users and many different programs to concurrently utilize available processor(s). This type of multi-user, multi-processing networking technology/protocol is the foundation of the Internet operations.

II. Modems

A user may access the Internet directly through a computer connected to a modem which is, in turn, interconnected to the Internet. Modems (modulator-demodulators) are input-output devices that translate back and forth between digital and analog communications. Modems allow computers (digital communicators) to "talk" to each other via a phone line (typically, an analog communicator). A modem on a computerized device at one end of a transmission line translates digital pulses into transmittable signals (such as analog signals/sound) for transmission to another, remotely-located computer through a fiber-optic or coaxial cable, telephone line/cable, or other remote-connection communication network (including a cellular satellite network). A modem connected to a computerized device at the other end of the transmission line reverses the process so that the data can be read.

III. The world wide-web ("www")

While the word 'Internet' generally refers to the multi-functional aspects of the communications medium/global network, "www" is used to describe the abstract space of knowledge, commonly 'webspace', on the Internet. The www works under the popular network computer model known as "client-server". A www server (or, web server) is a program running on a computer whose purpose is to serve documents or digital information to other computers upon request. A www (or 'web') client is a program generally run on the user's (client) computer so that the user can request digital information from the server (for example, browsers are considered web clients). Web servers are most-often remotely located from the computerized equipment running a web client. 'Remote' or other location as used in connection with the www, or any private/controlled WAN, or LAN, can mean hundreds-of-thousands of miles away, or simply upstairs in the same building (but interconnected to some type of local or global network).

IV. A Common Language

One popular communications protocol used by www clients and servers for purposes of communication is the Hyper Text Transfer Protocol (HTTP). All web clients and servers must be able to speak a common computer language in order to send and receive documents. Hence, web servers are often simply called HTTP servers. The standard format used for creating and recognizing hypermedia documents, or 'web pages', is the Hyper Text Markup Language (HTML). HTML is derived from another document formatting language used widely in publishing known as Standard Generalized Markup Language (SGML). The File Transfer Protocol (FTP) is one simple way to exchange files between computers on the Internet. Like HTTP (which transfers displayable web pages and related files) and the Simple Mail Transfer Protocol (SMTP which transfers e-mail), FTP is a standard communications protocol that uses Internet Protocol (IP). FTP is commonly used to transfer web page files from their creator to the computer that acts as their server. FTP is also commonly used to download programs and other files to a user's computer from FTP servers located at other locations.

V. FAXing and Hard-copies

To receive a document transmitted over a phone network (whether fiber-optic or coaxial cable, satellite cellular transmission, and so on) or via microwave relay, a facsimile machine (hereafter "FAX") or a FAX program operational on a processor in communication with a printing device, may be employed. The word facsimile refers to a process, system, or apparatus for reproducing hardcopy material at a distance. A drawing, page of text, or picture is scanned by a light-sensitive device to produce an electric signal which is typically sent through a phone network. In most earlier systems, the signal is an analog of the brightness of the graphic material being scanned. More sophisticated machines/software generate digital signals-streams of ones and zeros-that are coded and compressed versions of the analog signal. Solid-state technology allows FAX machines to utilize miniature photo-sensitive arrays to take an electronic snapshot of a document. Stand-alone FAX machines generally reproduce the received FAX-copy by employing photographic, electricity-sensitive, and thermal (heat-sensitive) paper. If the FAXed document is sent directly through a modem into PC memory, for example, later reproduction of the document may be done through a printer connected to the PC. There are many types of printers that can create a hardcopy of a document that has been received in memory: daisy-wheel, dot-matrix, laser, ink-jet printers, and thermal printers.

VI. Digital Computing

The apparatus and process of the invention are preferably carried out by incorporating a digital computer processing unit. The digital CPU is not the only computing processor suitable for use, however. By way of background, as is known, central processing unit (CPU) chips and microprocessors have four functional sections: (1) the arithmetic/logic unit, (2) temporary storage locations, called registers, which hold data, instructions, or the results of calculations; (3) the control section, which times and regulates all elements of the computer system and also translates patterns in the registers into computer activities; and (4) the internal bus, a network of communication lines that links internal CPU elements and offers several different data paths for input from and output to other elements of the computer system. Input devices let users enter commands, data, or programs for processing by the CPU. Many types of input devices are available: keyboards or specialized keypads, a mouse (a mechanical or optomechanical device with buttons and a rolling ball); joysticks and trackballs; light pens; touch-sensitive display screens (allow users to point to items or areas on a screen to activate commands); and voice-recognition circuitry exists that digitizes spoken words.

VII. Digital Computer Data Storage and Operation

Most digital computers store data both internally, in what is called main memory, and externally, on auxiliary storage units. As a computer processes data and instructions, it temporarily stores information internally, usually on silicon random-access memory, or RAM. Another type of internal memory consists of a series of read-only memory, or ROM, chips. Other devices that can be used for main memory are magnetic-core memory and magnetic-bubble memory. Four often used auxiliary storage devices—floppy disks, hard disks, magnetic tape, and magnetic drums—store data by magnetically rearranging metal particles on disks, tape, or drums. A LAN (Local Area Network) is a communications network that serves users within a confined geographical area, contained in a building or complex, and so on; whereas a WAN (Wide Area Network) is a communications network that covers a wider geographic area, such as state or country.

SUMMARY OF THE INVENTION

It is a primary object of this invention to provide a process and associated computerized system for tracking patient treatment rendered at a treatment location (whether on an in-patient or out-patient basis) by a provider, including any ancillary and primary health professional/provider trained to render skilled services to a patient. Included are features for entering, through an interactive/user interface, information/data concerning an evaluation or re-evaluation, the identification of functional goals associated therewith, generation of a plan (prescription of follow-up treatment or care), as well as progress made during a current treatment session/visit toward any then active goals (whether identified during the current treatment session). A treatment record is generated for storage for each active goal comprising progress made toward that goal during the current treatment session.

As will be more-fully appreciated, the advantages of the novel, flexible process and associated system and program code employed in connection therewith of the invention, include without limitation:

(A) Simplicity of design and use—A computerized apparatus of the invention with which a user can interface to enter data at the treatment location, host location, or some other convenient location, can be sized for portability or anchored if necessary. Furthermore, a user of the apparatus has at her/his fingertips through a user-friendly interactive interface, a panoply of information input displays to enter information concerning a treatment session according to the invention. The specific steps taken to carry out patient evaluation, goal identification, generation of patient plans, the rendering of services (preferably according to accepted tests using associated skilled-intervention/tools), and recording patient progress associated with then-active goals, are straightforward allowing for continuity of care. Control of computer operation and maintenance can be centralized by use of a main, or host, location for the server/host computer.

(B) Speed and accuracy—Eliminating the need for manual, labor-intensive generation of various reports seeking authorization of payment from payors, saves time and can substantially decrease human error in payment processing; furthermore, a more-unified series of reports can be generated, transmitted, and/or printed to include a variety of different types of information concerning patient treatment over a selected period of time.

(C) Versatility of operation—The system and process of the invention are operable with a wide range of computer operating systems and a wide range of computer network environments whether used locally (LAN) or over a worldwide network (WAN), such as the Internet, to transmit information.

(D) Design flexibility—The computerized apparatus with which a provider of services, or data entry clerk, interfaces (such as a personal computer, "PC", workstation, or other high-end client) can be programmed and/or loaded with applications so that it may handle additional automatic tasks. Also, a remote host server or system of interconnected servers (whether or not each is independently-operational) may be readily programmed using known suitable programming tools and techniques (including subroutines, program modules, etc.).

(E) Ready implementation of invention—Off-the-shelf programs/applications to control components of the computerized apparatus, along with web servers and associated interface protocols, communication protocols and security functionality, existing telecommunications cable/links, and any equipment used to scan and produce hard copies of documents, may be utilized in carrying out the features of the invention.

Briefly described, once again, the invention includes a process for tracking skilled-service rendered a patient by a provider at a treatment location. At the treatment location, at least one record of progress is generated for the progress made toward each treatment goal identified for the patient and addressed by the provider during the session. Next, an input comprising each record of progress so generated, is received for storage as treatment record data at a host location. Preferably the data is stored in searchable data fields for access and retrieval upon command. Using the treatment record data and a host processor, a patient report can be automatically generated for submitting to an entity selected from the group consisting of a health care facility, a health care provider, an insurer, the patient, an entity authorized to receive records of the patient, and a record-keeping entity for the provider. A composite record of each record of progress/outcome, along with a record of skilled intervention used, may be generated at the treatment location by filling-in a hardcopy form or entering the information in respective input fields of an electronic display form.

The record of progress can contain information such as: a description of the goal, for example, using searchable key terms or phrases taken from a list of standard acceptable outcomes; a date the treatment session took place; the patient's and the provider's entities; and a description (using searchable key terms and phrases, for example) of the progress made as observed during that session. The information is preferably entered into respective input fields of a treatment record display via suitable interface located at the treatment location, the host location, or any other suitable data entry location. Each treatment goal identified is preferably based upon an evaluation of the patient's condition. The evaluation may take place prior to, or during, the current treatment session, by the same or another provider—and can be input for storage as evaluation record data. A plan comprising a prescription for follow-up with the patient is preferably generated and can be entered into an input field of a plan record display for storage as plan record data. A provider with access to an interface at which plan and evaluation displays are viewable may pull up associated plan and evaluation records of the patient during the treatment session; alternatively, a hardcopy of a plan and evaluation earlier generated may be printed and used at the treatment location.

Another characterization of the invention includes a system including a composite record generated at the treatment location of at least one record of progress made during the session, a storage medium at a host location for storing searchable treatment record data comprising each record of progress, and a host processor for automatically generating, using the treatment record data, a patient report for an entity selected from the group consisting of a health care facility, a health care provider, an insurer, the patient, an entity authorized to receive records of the patient, and a record-keeping entity for the provider. The composite record, which can include a plurality of records of progress in the event more than one goal is addressed by the provider during the treatment session, can further include a plan for follow-up with the patient.

A further characterization includes a computer executable program code on a computer readable storage medium for tracking skilled-service rendered a patient by a provider at a treatment location. The program code to include: a first program sub-code for receiving an input of data comprising at least one record of progress made toward each treatment goal identified for the patient and addressed by the provider at the treatment location during a treatment session; a second program sub-code for storing each record of progress so received, as treatment record data at a host location; and a third program sub-code for generating a patient report using the treatment record data and a host processor. The patient report includes information from the at least one record of progress for submitting to an entity selected from the group consisting of a health care facility, a health care provider, an insurer, the patient, an entity authorized to receive records of the patient, and a record-keeping entity for the provider.

The patient report can be transmitted by way of compatible data transfer pathway to the entity for: seeking timely payment for the skilled-service rendered; record-keeping; reporting patient progress and condition to another health care provider or health care facility at which the patient is temporarily residing; and the like. The data transfer pathway can be any of a number of mechanisms for transferring information in the form of a patient report generated automatically using a processor.

BRIEF DESCRIPTION OF THE DRAWINGS

For purposes of illustrating the innovative nature plus the flexibility of design and versatility of the innovative technique and system disclosed hereby, the invention will be better appreciated by reviewing the accompanying drawings (in which like numerals, if included, designate like parts). One can appreciate the many features that distinguish the instant invention from known techniques. The drawings have been included to communicate the features of the innovative system and associated technique of the invention by way of example, only, and are in no way intended to unduly limit the disclosure hereof.

FIG. 2C depicts a sample admin. information display (block 2C in FIG. 1).

FIG. 2D depicts a sample evaluation information display (block 2D in FIG. 1).

FIGS. 2E and 2F illustrate input formats (as displays or hardcopy 25A and 25B) of a sample composite record generated at the treatment location, by way of example.

FIG. 3 depicts a sample treatment record display 30 having input fields that accommodate, for example, two records of progress-each associated with a goal.

FIG. 6 depicts a sample evaluation record display 60 having input fields that accommodate, for example, two evaluation records.

DESCRIPTION OF ATTACHMENT A

The enclosure labeled ATTACHMENT A is hereby fully incorporated herein by reference to the extent necessary to aid in an understanding, and in further support, of the invention. The 18 pages of ATTACHMENT A depict further examples of the displays and reports/summaries identified in FIG. 1 and labeled according to respective higher-level information displays (REPORTS, ADMINISTRATION, and EVALUATION/ADMINISTRATION) from which they are accessed: accessible from REPORTS display 2B are those labeled $B_1$-$B_7$, accessible from ADMINISTRATION 2C are those labeled $C_1$-$C_6$, and accessible from EVALUATION/ADMIN 2D are those labeled $D_1$-$D_4$.

DETAILED DESCRIPTION OF THE EMBODIMENTS

Figure 1:
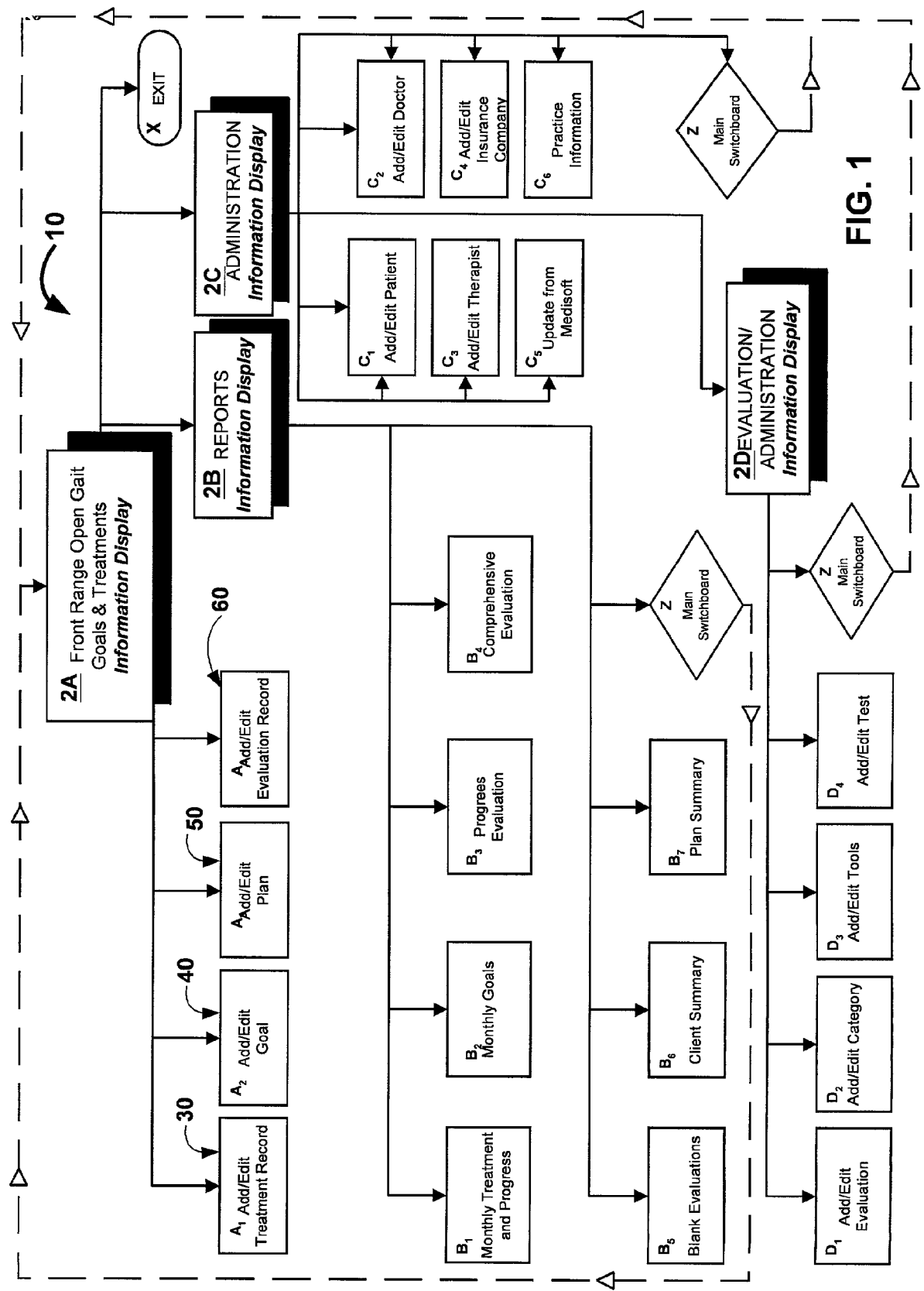
FIG. 1 diagrammatically illustrates a preferred system of interconnected displays and patient-related reports/summaries, each of which is labeled for reference.
Figure 2A:
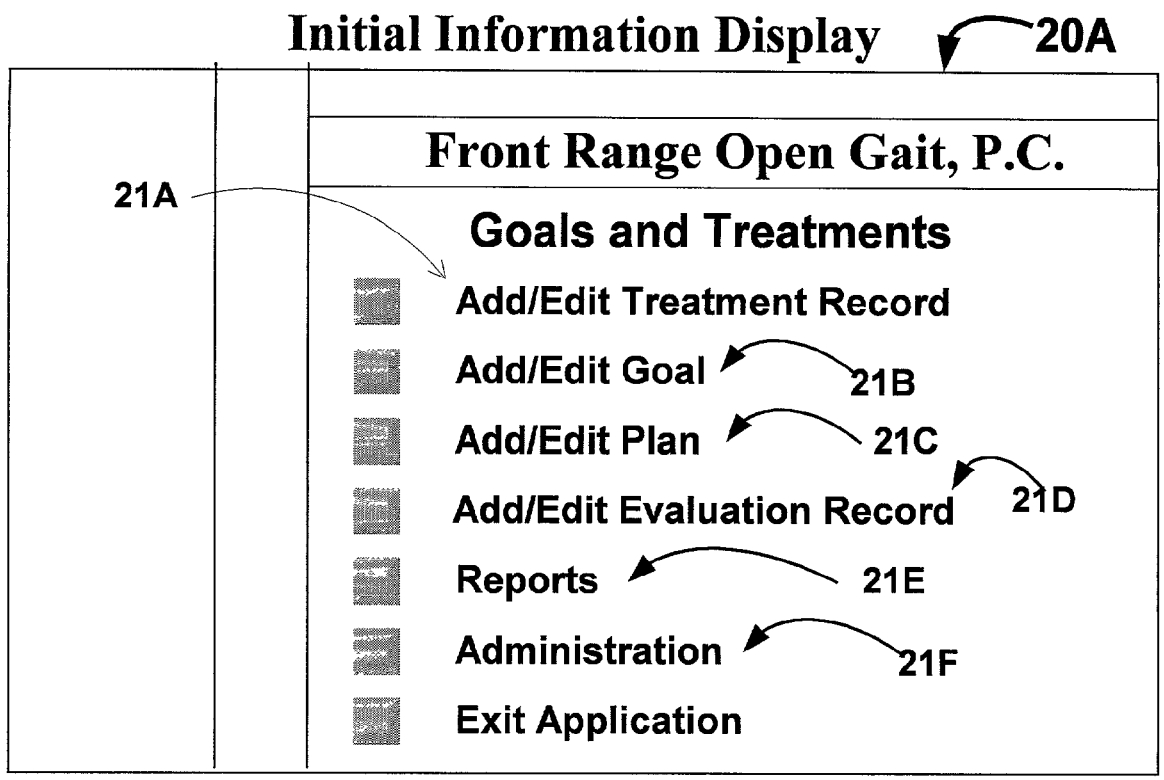
FIG. 2A depicts a sample initial information display (block 2A in FIG. 1).
Figure 2B:
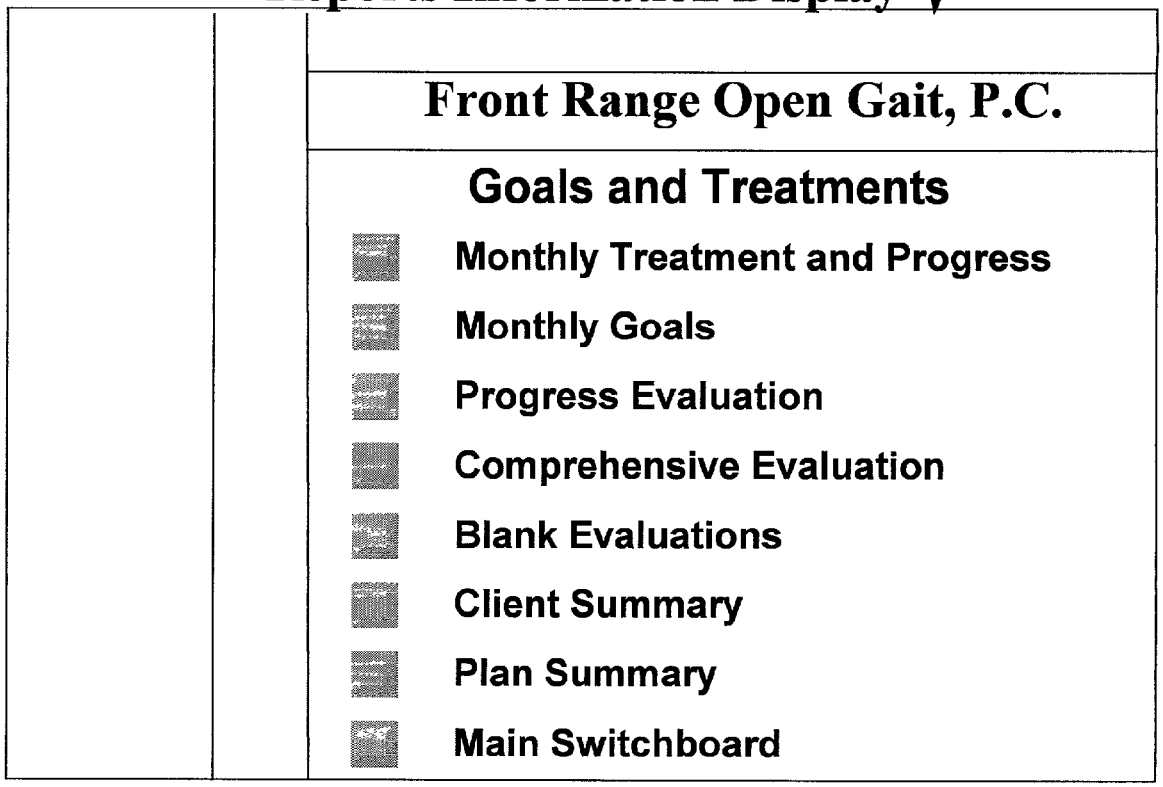
FIG. 2B depicts a sample reports information display (block 2B in FIG. 1).

As mentioned above in connection with ATTACHMENT A, FIG. 1 diagrams the accessibility of information displays and patient reports organized according to higher-level information displays from which they are accessed. In addition to providing access to higher-level displays 2B, 2C, and 2D, initial information display 2A allows a user to access displays shown in FIGS. 3-6, respectively, as 30, 40, 50, and 60. In all cases, the higher-level information displays allow for returning to the initial display 2A via a "Main Switchboard" icon Z (no example is included). FIG. 2A depicts a sample initial information display 20A—this is depicted in FIG. 1 as block 2A. By engaging (by way of, for example, a double-click with a mouse) icons 21A-21F, one is allowed to move from display 20A through to respective displays such as those depicted herein: Add/Edit Treatment Record 21A will access a FIG. 3 display 30; Add/Edit Goal 21B will access a FIG. 4 display 40; Add/Edit Plan 21C will access a FIG. 5 display 50; Add/Edit Evaluation Record 21D will access a FIG. 6 display 60; Reports 21E will access a FIG. 2B display 20B; and Administration 21F will access a FIG. 2C display 20C (which, in turn, allows for access to display 20D for Evaluation/Reports).

FIGS. 2E and 2F illustrate input formats (in the form of active displays or alternatively as hardcopy, 25A and 25B) of a sample composite record generated at the treatment location. By way of example only, spaces 29A-29C are provided for recording specific progress made toward three respective goals (identified from a non-exhaustive suggested listing 26L targeted to a therapy discipline) during a treatment session. Space for recording information about the type of skilled-intervention used to address each goal during the session is provided at 28A-28C. The listing 26L is included in the composite record format shown for handy reference allowing for greater consistency of treatment between providers. Preferably, a provider who initially selects (shown at 26g) a general goal description from the listing, will tailor it to the patient based upon an evaluation, or re-evaluation, of the patient's condition and accordingly use skilled intervention (28A-28C). Progress made during the treatment session is first recorded in space provided at 29A-29C and a change in the patient's plan or prescription for follow-up is recorded at 56CH. On both displayed forms 25A and 25B there is space for the provider to identify his/herself.

Information entered onto/into 25A and 25B can be transferred or transmitted into respective input fields of treatment records, goal records, and plan records for storage as searchable and retrievable data at the host location. For example, if 25A and 25B displays are in hardcopy form, entry by a data entry specialist, scanning, or other suitable means, is performed to transfer the information into electronic form. If 25A and 25B are active displays, information can be entered via, for example, user interface at the treatment location (e.g., keypad, electronic pen/touch-sensitive screen, keyboard, mouse, etc., and any combination thereof), and temporarily stored or held at the treatment location for later download via interface through a host processor to more-permanent storage at a host location, or actively transmitted via WAN (such as the Internet) or LAN as the information is entered, otherwise held and transferred to the host location storage.

FIG. 3 depicts a sample treatment record display 30 having input fields 38A and 38B that accommodate, for example as shown here, two records of progress—each associated with a respective goal described in field 36A and 36B. Each of the two treatment records illustrated comprise information concerning a goal, as follows: a description of the goal (36A, 36B); treatment date (32A, 32B); the provider's identify (35A, 35B); patient identity (34A, 34B); session length (33A, 33B); and narrative of progress made during the session (38A, 38B). Also included for each treatment record is a document screen admin tool bar area (31A, 31B) to request a search of All records for inclusion in the active display, plus icons for paging through those records as well as opening a new record for data entry. By way of example, information about each goal selected (list 26g in FIG. 2F) is entered in short narrative tailored to the patient, into fields 36A, 36B (FIG. 3); and information from 29A and 29B (entered into form 25B, FIG. 2F) is entered into fields 38A and 38B (FIG. 3).

Figure 4:
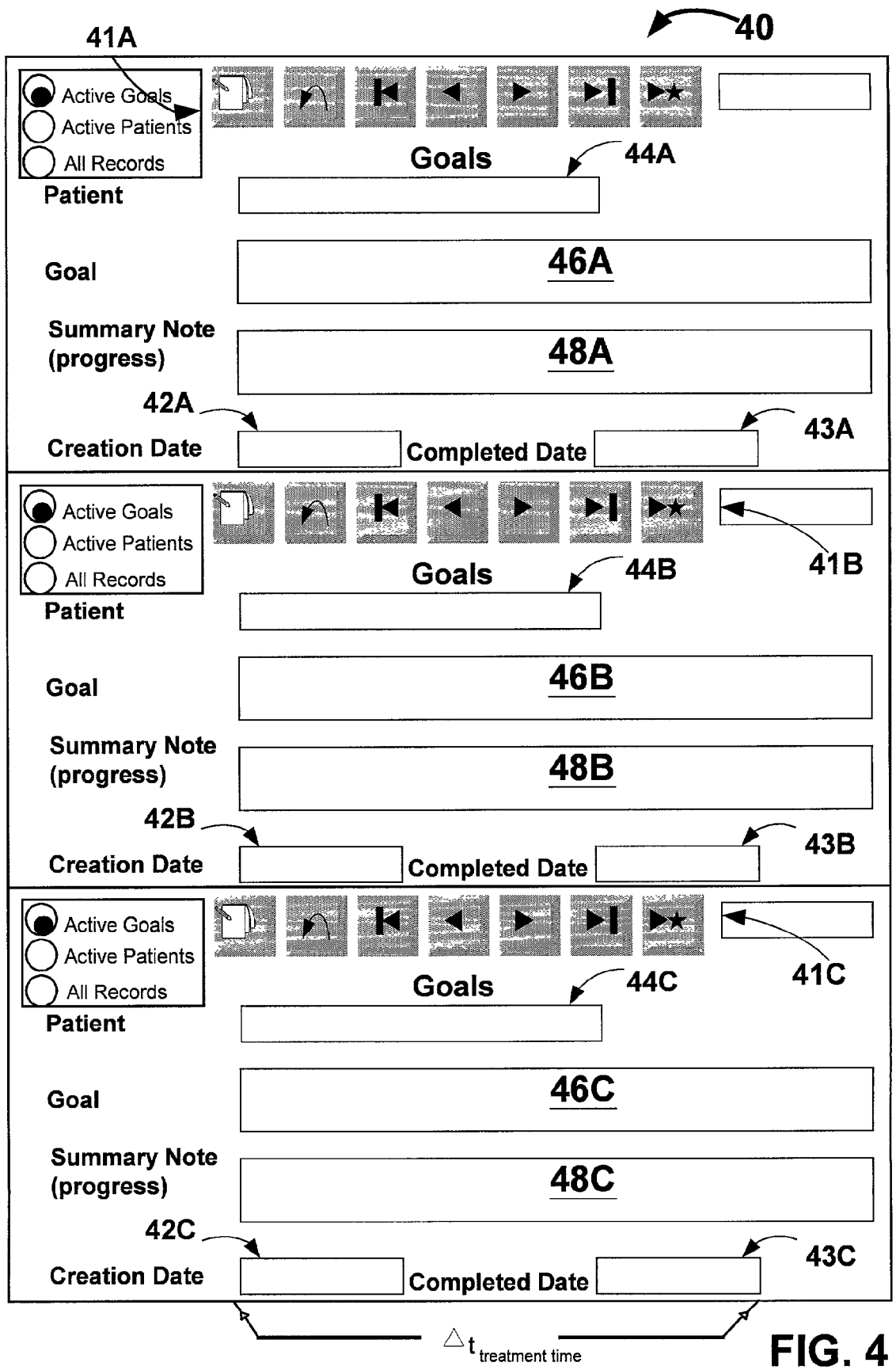
FIG. 4 depicts a sample goal record display 40 having input fields that accommodate, for example, three records of progress status ("Summary Note")—each associated with a goal (input fields 46A-46C allow for description of each goal).

FIG. 4 depicts a sample goal record display 40 having input fields that accommodate, for example, three records of progress status ("Summary Note")—each associated with a goal (input fields 46A-46C allow for description of each goal) for later search and retrieval. Display 40 allows the provider, or another with authorized access to the patient's records, an automated mechanism by which information concerning a goal may be entered at a later, more-convenient time. Each of the goal records illustrated in display 40 comprise information, as follows: a description of the goal (46A-46C); a narrative of progress made (48A-48C); date the record was generated (42A-42C); completion date, if any, when goal has been met (43A-43C); patient identity (44A-44C); and associated document screen admin tool bar area (41A-41C) to request a search of Active Goals, Active Patients, or All Records for inclusion in the active display, plus icons for paging through those records as well as opening a new record for data entry. By way of example, information about each goal selected (list 26g in FIG. 2F) is entered in short narrative tailored to the patient into fields 46A-46C (FIG. 4) and associated progress made from 29A-29C (form 25B in FIG. 2F) is entered as a short narrative into fields 48A-48C (FIG. 4).

Figure 5:
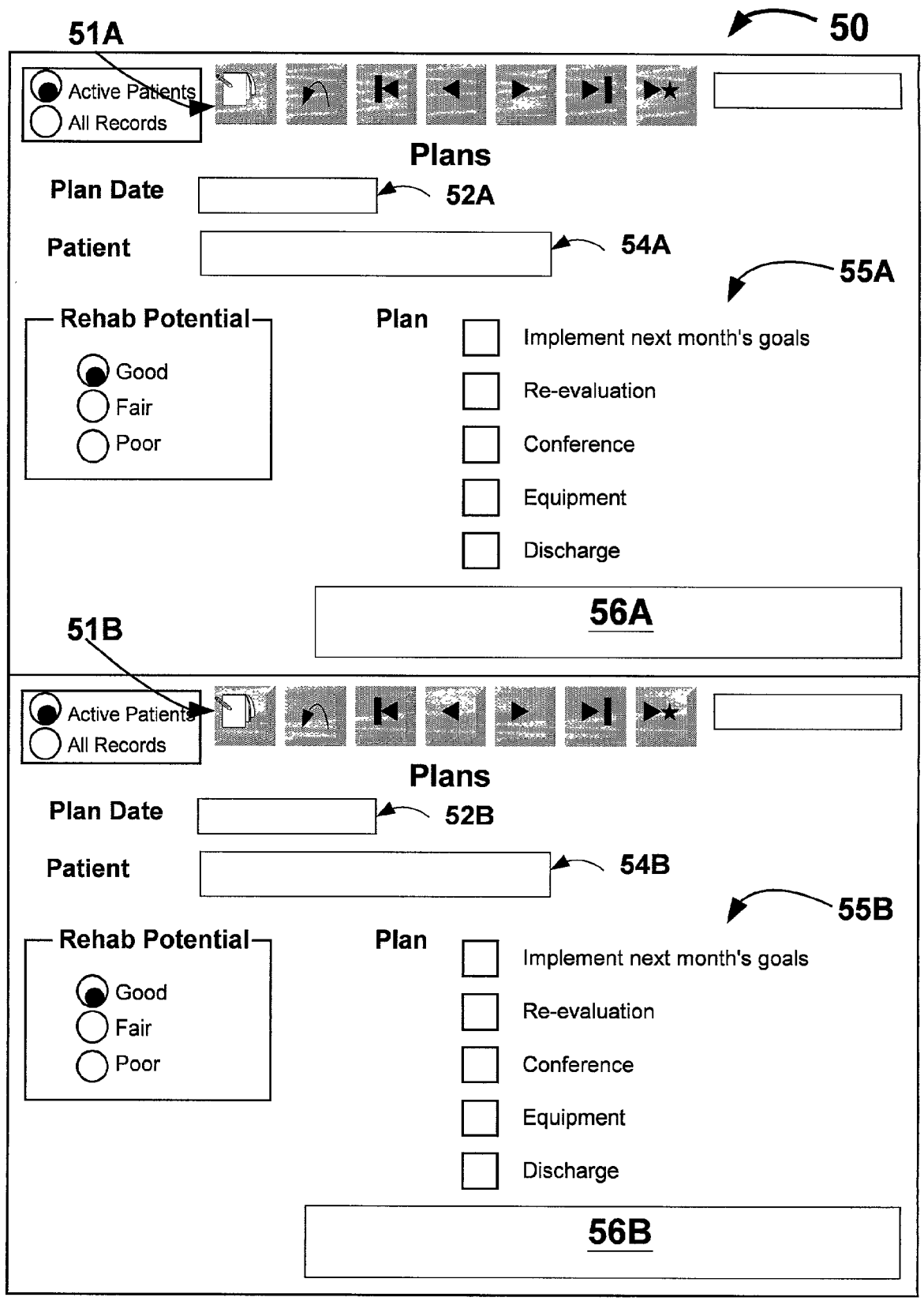
FIG. 5 depicts a sample plan record display 50 having input fields that accommodate, for example, two plan records.

FIG. 5 depicts a sample plan record display 50 having input fields that accommodate, for example, two plan records. Display 50 allows the provider, or another with authorized access to the patient's records, an automated mechanism by which a plan record may be changed, updated or new plan initiated, any convenient time after a treatment session. Each of the plan records illustrated in display 50 comprise information, as follows: a description or narrative of the plan (56A, 56B); date the respective plan was generated (52A, 52B); suggested listing of future action connected with that plan (55A, 55B), patient identity (54A, 54B), and associated document screen admin tool bar area (51A, 51B) to request a search of Active Patients or All Records for inclusion in the active display, plus icons for paging through those records as well as opening a new record for data entry. By way of example, information about each plan or change in plan generated at the treatment location (from field 56CH in FIG. 2F) is entered into fields 56A, 56B.

Figure 6:
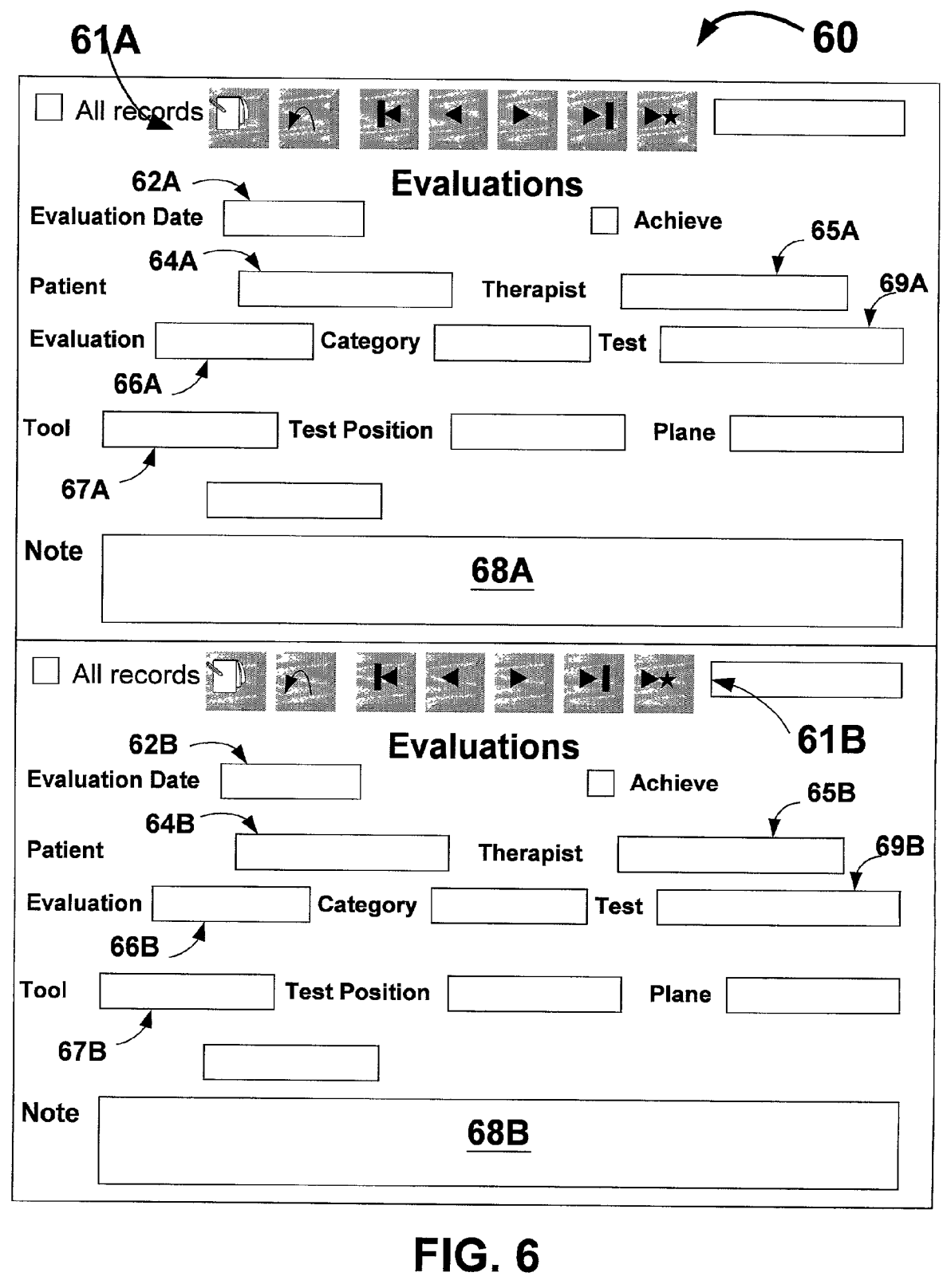

FIG. 6 depicts a sample evaluation record display 60 having input fields that accommodate, for example, two evaluation records. Display 60 allows the provider, or another with authorized access to the patient's records, an automated mechanism by which information concerning an evaluation may be entered at a later, more-convenient time. Each of the evaluation records illustrated in display 60 comprise information, as follows: evaluation identification (at 66A-66B, 67A-67B, and 69A-69B, these input fields can include terms generally used in a particular therapy or treatment discipline); additional narrative of the evaluation (68A-68B); date the evaluation was done (62A, 62B); patient identity (64A, 64B), provider identity (65A, 65B); and associated document screen admin tool bar area (61A, 61B) to request a search of All Records for inclusion in the active display, plus icons for paging through those records as well as opening a new record for data entry. By way of example, information from 28A and 28B (entered into form 25B, FIG. 2F) relating to patient evaluation can be entered into respective input fields 68A and 68B (FIG. 6) used as, or to supplement, the narrative indicated in FIG. 6 as "Note".

Figure 7:
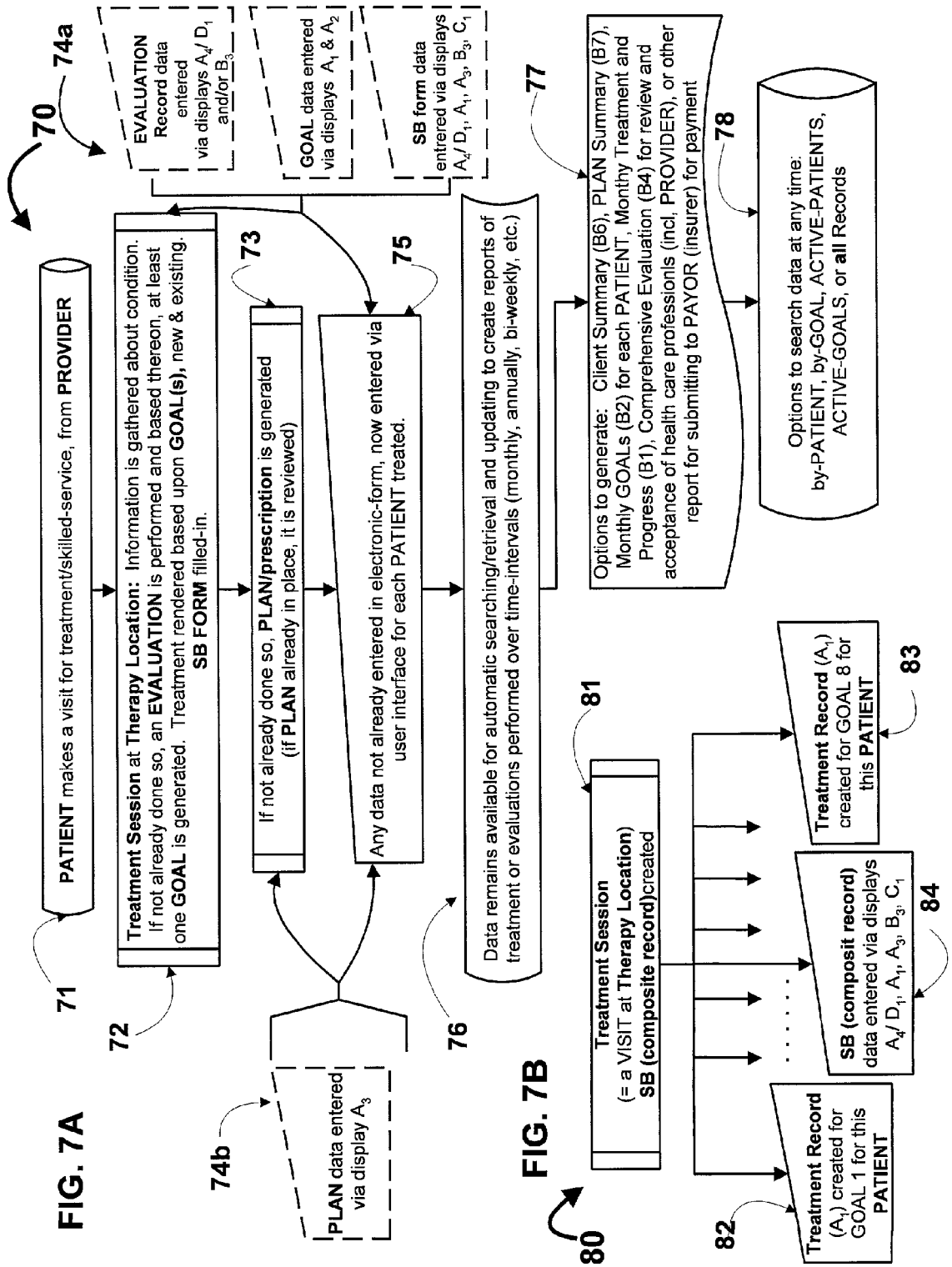
FIG. 7A depicts, in process flow diagram format, a method of the invention including detail of preferred points of data entry.
FIG. 7B is a block diagram further detailing the type of information recorded and entered in connection with a treatment session/patient visit.

FIG. 7A depicts, in process flow diagram format at 70, a method of the invention including detail of preferred points of data entry. Patient with a condition, problem, ailment, or impairment makes a visit for a skilled-service of some sort from a provider—one or more individuals (therapist and associate, doctor and nurse, etc.) trained in a treatment or therapy discipline (71). During a treatment session or visit at a therapy location (whether on-site at a traditional health care facility or off-site at any number of locations where treatment/therapy can be rendered) information is gathered about the patient's condition (72). If not already done so, an evaluation of the patient's condition is performed and based thereupon at least one goal is identified for tracking results of skilled-intervention used. At the treatment location, at least one record of progress made toward the identified goal is generated. A plan including a prescription for follow-up activity/skilled-service of the patient is generated (73). Data entry of information into respective input fields of records is performed (75) covering evaluation performed, goals identified, and progress made toward those goals, as well as other information for which space is provided, for example, in the composite records labeled 25A and 25B (FIGS. 2E and 2F)—opportunities for doing so are referenced in FIG. 7A at 74A, 74B.

FIG. 7B is a block diagram further detailing the type of information recorded and entered (81) in connection with a treatment session/patient visit (such as is represented by process step 72 of FIG. 7A). Referenced at 82 and 83 are the treatment record(s) depicted in FIG. 3 and referenced at 84 is the composite record generated at the treatment location, an example of which is depicted in FIGS. 2E and 2F.

Figure 8:
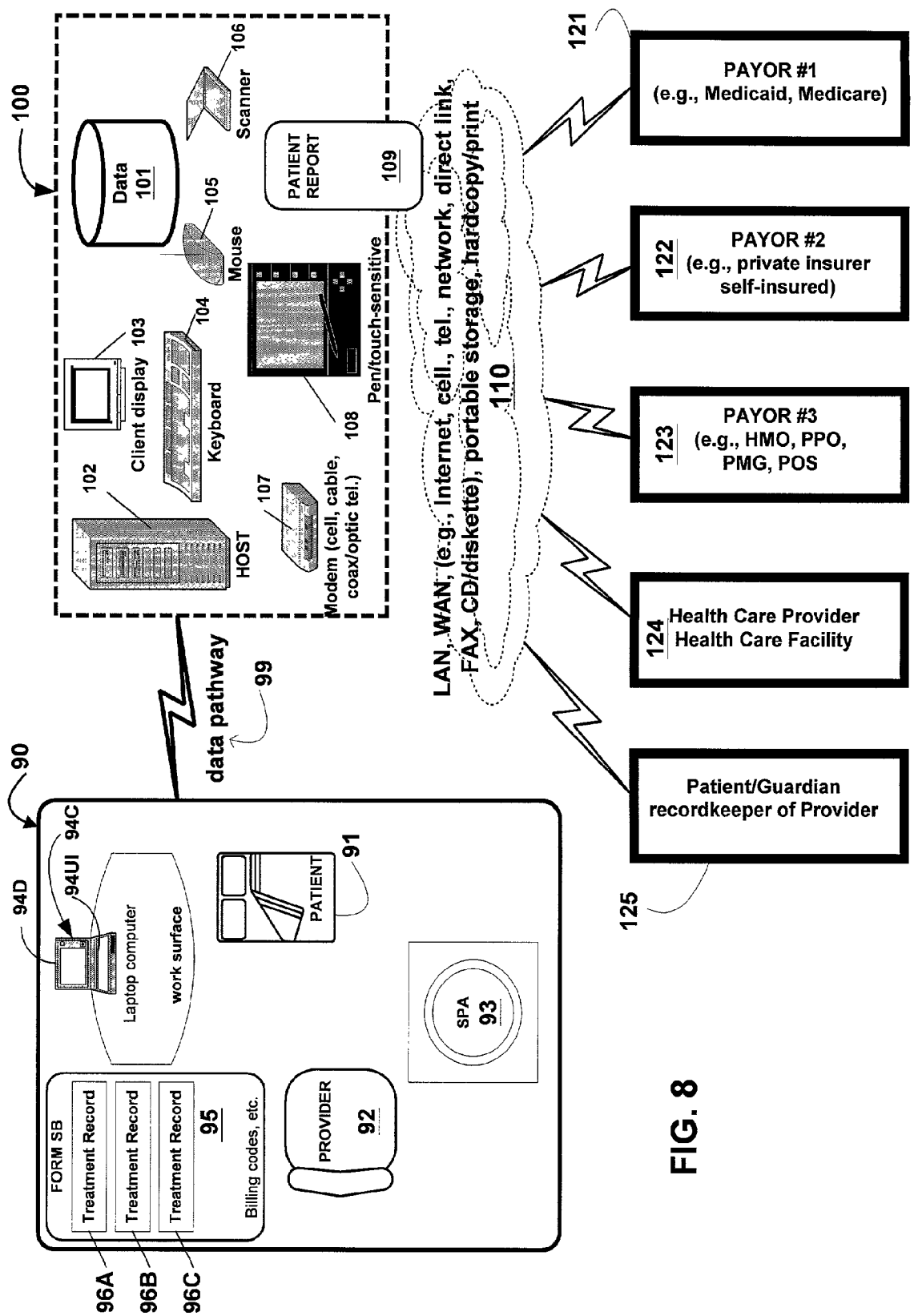
FIG. 8 diagrammatically illustrates feature details, including interconnection, of components of a system of the invention.

One can truly appreciate the flexibility of design and versatility of use of the invention from the FIG. 8 diagrammatical representation of a preferred system detailing the interconnection of components. A location or site for treatment/therapy or other ancillary health care related services is depicted by a boundary labeled 90. Information concerning the patient, any evaluation or re-evaluation made, goal(s) identified, skilled-intervention used, progress made toward identified goal(s), plan for follow-up with the patient, the provider's identity, date of treatment session, requisite billing codes, etc., is generated and preferably initially recorded (95) at the treatment location while the information is 'fresh' in the mind of the provider 92. This information (95) may be manually entered into a format such as those labeled 25A and 25B (FIGS. 2E and 2F) whether handwritten or input into fields via user interface (display 94D or keyboard/pad 94UI) of a computerized device (such as computer 94C). For reference simply to indicate a skilled-intervention, an item labeled "SPA" is shown within the treatment location 90. A data transfer pathway 99 is interposed between the treatment location 90 and host location 100. A patient report identified at 109 is generated and output (in hardcopy or electronic form) from host location 100 for submission to an entity through a second data transfer pathway represented at 110 as a mechanism for providing access to various entities including prospective PAYORs (labeled 121, 122, and 123), as well as heath care providers and health care facilities (labeled 124) and/or patient or other entity authorized to receive patient records plus a record keeper of the provider 125.

Treatment record data, comprising treatment records represented at 96A-96C of a patient's (91) progress during a treatment session at a treatment location 90, are retrieved from a storage (101) and used to automatically generate a variety of reports (109) in a systematic manner for submission (via suitable transfer or transmission 110) in connection with a range of purposes such as to seek reimbursement from, or report patient progress to, any one or more of the following: a physician, dentist, or other primary or ancillary health care provider caring for the patient (124); a hospital, out-patient clinic, laboratory/testing center, nursing home, or any other health care facility (124); an HMO, PMG, PPO (under an auto insurance plan, for example), POS group, or any other managed care organization (123); a private medical insurance carrier (122); government-sponsored or supported insurance such as Medicaid and Medicare (121); the patient, his/her legal guardian, or other person with authorization to obtain the patient's records (125); an entity that maintain records for the provider (125); and so on. Confidential reports (109) can be generated as contemplated according to the invention, these include reports containing, by way of example only: goals identified over a select time period, e.g., monthly, weekly, daily, or per-session, for a particular patient; progress made over a selected time period, e.g., semiannually, monthly, or biweekly, weekly, daily or per-session, toward meeting active goals for a patient; comprehensive evaluation for submission to a health care provider or facility (clinic, hospital, etc.); treatment plan or prescription summary for a patient; summary of all active and completed goals for all current and discharged patients, or a select subset thereof, of the provider treated over a select time period, e.g., monthly or semiannually; as well as other reports tailored (e.g., patient- or provider-specific) to include information from the searchable display fields into which data has been entered and stored.

A processor (102) and associated storage (101) and memory (102) are employed in communication with suitable interactive interface (such as client display 103, keyboard 104, mouse 105, scanner 106, and pen/touch-sensitive screen 108 at the host location 100) or other interface such as laser terminal, diskette-, CD-, or tape-drive, or other interface for accepting electronic data from temporary storage or temporary memory of portable computer 94C at the treatment location, for entry of data into designated searchable data fields for automatic compilation of current treatment session data with any prior treatment information to create records for each patient for which biographical-type information has been entered. The technique and system of the invention incorporate the unique features embodied especially within and between 99, 100, 110, for automatically generating reports requested by a multitude of separate payors from whom payment is eventually sought by the provider once treatment has been rendered. As a result of each treatment session, each identified goal (whether generated at this treatment session or as a result of a prior session) will have a Treatment Record 96A-96C generated therefor (such as those depicted in FIG. 3) interconnecting all progress made by the patient associated with a respective identified goal during the current treatment session. A diagrammatic representation 80 of sample records generated in association with a treatment session, or visit, is shown in FIG. 7B. FIG. 1 graphically illustrates the interconnection of displays and reports which one may generate and submit, automatically (such as by way of LAN, WAN, modem into and through the Internet, etc.) to an entity such as a prospective payor for payment, whether as a hardcopy for filing with the provider's patient records or as electronic data.

Any reports generated (109) and submitted via 110 to an entity such as a prospective payor (including an insurer of the patient) for payment of skilled-services rendered, if accepted by the payor, will preferably result in payment to the provider. Any suitable means may be used to effectuate the present receipt of legal tender in an amount equal to an amount due the provider for its skilled-services rendered, whether or not made automatically, including an electronic transfer of funds/direct deposit into an identified bank account, an e-record of a draft in the amount due sent electronically and printable at the provider's hose location 100 a draft printed at the payor's location (121-125) and mailed, an account of the payor's charged for later collective payment on a monthly basis, SSL transaction over the internet or other WAN using a credit or debit card, and so on.

The invention utilizes a unique and flexible, yet simplified, computerized technique to track treatment rendered based upon functional goals tied to a clinical evaluation and automatically generate reports for submission to a payor for payment of skilled services rendered (allowing for transmission of data back and forth permitting an automatic authorization and if given, in turn automatically effectuate the present receipt of the legal tender to the provider in the authorized amount). Both the process and associated system have been designed for user-friendly operation (see, for example, ATTACHMENT A depicting additional information displays and reports). As one can appreciate, within the spirit and scope of design goals contemplated hereby, the new computerized authorization system and associated process are operable with a wide range of computer operating systems (most notably UNIX, LINUX, MS-DOS™-, MS WINDOWS™-, and MACINTOSH®-compatible) and a wide range of computer network environments whether used over a local area network (LAN), a wide area network (WAN) including one that accommodates phone transmission, HTTP, microwave relay, etc. The innovative process and system offer a unique combination and process flow of mechanisms for reporting to and seeking automatic payment/reimbursement.

Figure 9:
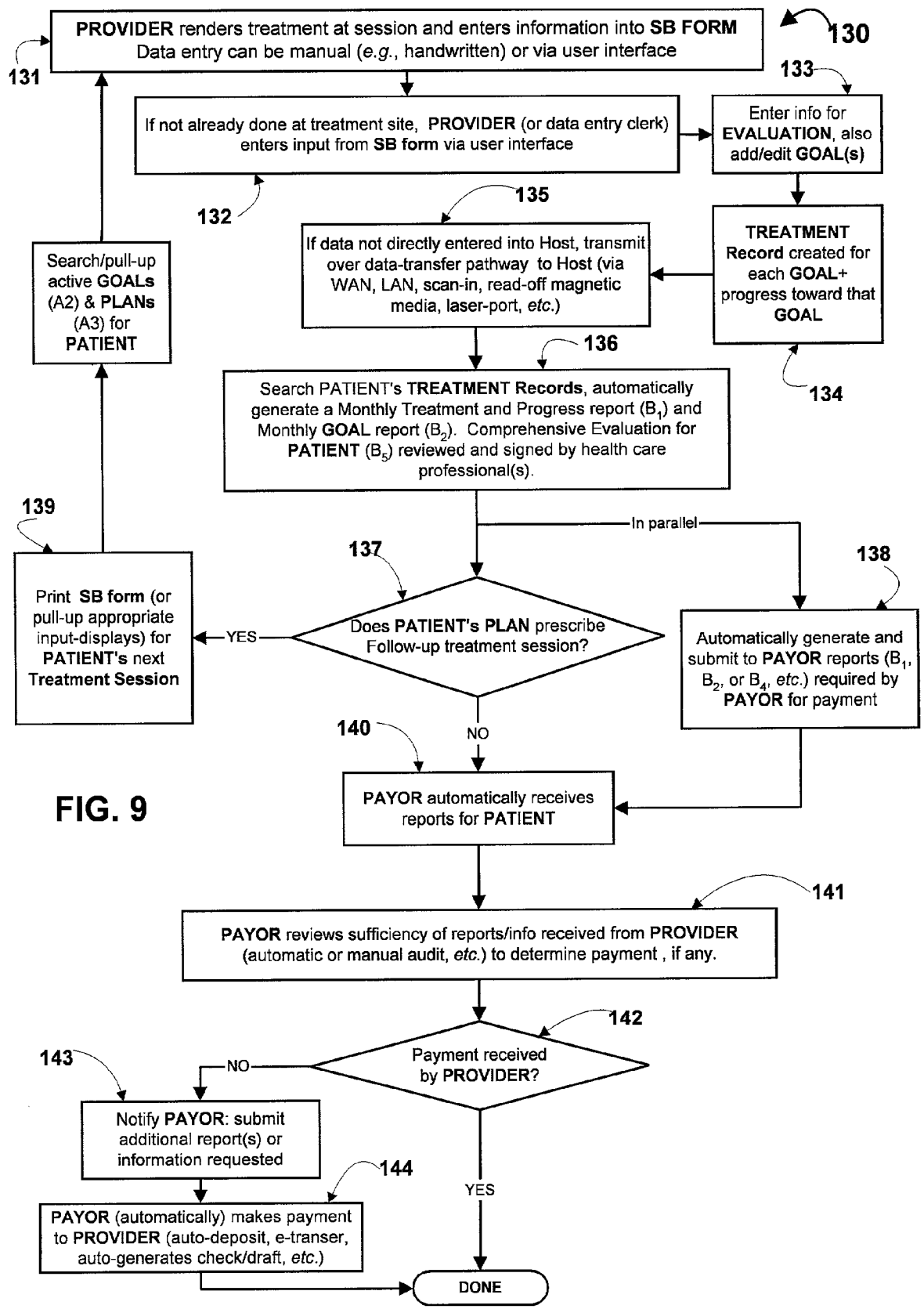
FIG. 9 is a flow diagram of process features/steps associated with the system.

FIG. 9 is a flow diagram of process features/steps associated with the system depicted diagrammatically in FIG. 8 as well as the system of displays in FIG. 1 (details of which are included in FIGS. 2A-2F and 3-6) and data entry opportunities depicted in FIGS. 7A-7B. As one can appreciate, the new process (130, FIG. 9) and associated system were developed for continuity of tracking and reporting treatment rendered, leading to a more efficient avenue of automatic reporting to others such as payors when seeking authorization and payment therefrom for skilled services rendered by a provider, while at the same time providing for overall continuity of care associated with diagnoses made. Unlike the labor-intensive processes currently available, the new system and process require much less human intervention by a provider as well as the provider's accounting/ admin departments, as well as any prospective payor. A provider renders treatment and generates a record thereof (131); data is entered 132 including information concerning evaluation, goals, progress made toward those goals (133, 134). Data is transmitted or otherwise entered into a host processor for storage (135). On an as-needed basis, patient's records can be searched and reports generated for submission and/or signature to others (136). If patent's plan provides for follow-up treatment (137), a composite record can be easily generated and either printed (139) or transmitted for use at the next session (may be the same or a different provider). Reports can be generated and submitted in parallel with follow-up treatment (138). The entity to whom report is sent receives it (140) and preferably makes prompt payment (141). If not (142), additional information may be provided to the entity about the patient (143) for payment (144).

By way of further reference as background: The central processing unit (CPU) is the computing part of the computer. Also often referred to simply as the processor, a CPU it is made up of the control unit and an arithmetic logic unit (ALU)—a high-speed circuit that does calculating and comparing. Numbers are transferred from memory into the ALU for calculation, and the results are sent back into memory. Alphanumeric data is sent from memory into the ALU for comparing. The CPUs of almost all computers are contained on a single chip. As is well known, the basic elements of a simple computer include a CPU, clock and main memory; whereas a complete computer system requires the addition of control units, input, output and storage devices, as well as an operating system. Computer professionals involved with mainframes and microcomputers sometimes refer to the whole computer as the CPU, in which case, CPU refers to the processor, memory (RAM) and I/O architecture (channels or buses). Once the data is in a computer's memory, the computer can process it by calculating, comparing and copying it; generally understood as follows: calculating— performing any mathematical operation on data by adding, subtracting, multiplying and dividing one set with another; comparing—analysis and evaluation of data by matching it with sets of known data that are included in a program or called in from storage; and coping—the moving of data around to create any kind of report or listing, etc., in a selected order. A data field is a physical unit of data that is one or more bytes in size; a collection of data fields make up a record. A field also defines a unit of data on a source document, screen or report, as is the case for fields such as NAME, ADDRESS, QUANTITY and AMOUNT DUE. When a user interactively queries and updates a database, data is referenced by field name. Other terms that refer to the same unit of storage as a field: A data element is the logical definition of the field, and a data item is the actual data stored in the field. An input field of a user interface such as a display screen is a common denominator, of sorts, between the user and the computer allowing for information to be accepted by the interface for storage.

While certain representative embodiments and details have been shown merely for the purpose of illustrating the invention, those skilled in the art will readily appreciate that various modifications, whether specifically identified herein, may be made to these representative embodiments without departing from the novel teachings or scope of this technical disclosure. Accordingly, all such modifications are intended to be included within the scope of the claims. Although the commonly employed preamble phrase "comprising the steps of" may be used herein, or hereafter, in a method claim, the Applicants do not intend to invoke 35 U.S.C. Section 112 §6. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. A process for tracking skilled-service rendered to a patient at a physical therapy treatment location by a physical therapy provider trained in a physical therapy discipline, comprising the steps of:

treating said patient based on at least one physical therapy treatment goal at said physical therapy treatment location by said provider;

generating at least one record of incremental provider observed progress development, said record of incremental provider observed progress development comprising an indication of incremental patient advances made toward a composite physical therapy treatment goal as compared to a preferred result;

evaluating development of said patient during at least one treatment modality based on said at least one physical therapy treatment goal during a treatment session;

dynamically modifying said composite physical therapy treatment goal to create at least one edited treatment goal identified for the patient based upon a development evaluation of said patient during at least one treatment modality;

receiving an input comprising at least one of said record of incremental provider observed progress development so generated, for storage as treatment record data at a host location;

using said treatment record data and a host processor, automatically generating a patient report; and submitting said patient report to an entity selected from the group consisting of a health care facility, a health care provider, an insurer, the patient, an entity authorized to receive records of the patient, and a record-keeping entity for the provider.

2. The process of claim 1 wherein: said at least one record of incremental provider observed progress development further comprises a description of said composite physical therapy treatment goal, a date of a treatment session, and the provider's identity; said step of receiving an input further comprises receiving said description and said provider's identity into respective data fields; and said step of submitting further comprises submitting said report for a payment from said entity for the skilled-service rendered.

3. The process of claim 1 wherein: said at least one record of incremental provider observed progress development further comprises a description of said composite physical therapy treatment goal and a date of a treatment session; said step of generating further comprises entering said incremental provider observed progress development made and said date into respective input fields of a treatment record display; said step of submitting further comprises transmitting said report as electronic data over a data transfer pathway to said entity for a payment for the skilled-service rendered.

4. The process of claim 1 wherein said physical therapy treatment goal was identified based upon an evaluation of the patient's condition, and said step of generating further comprises entering said at least one record of incremental provider observed progress development onto a hardcopy composite record; and further comprising, thereafter, the step of entering said incremental provider observed progress development made and a date of a treatment session into respective input fields of a treatment record display.

5. The process of claim 1 wherein said physical therapy treatment goal was identified based upon an evaluation of the patient's condition; and further comprising, prior to the step of automatically generating said patient report, the step of generating a plan comprising a prescription for follow-up with the patient.

6. The process of claim 5 further comprising the steps of:
generating an evaluation record comprising a description of said evaluation, a date of said evaluation, and a evaluator's identity; and
receiving an input comprising said evaluation record for storage as evaluation record data at said host location.

7. The process of claim 6 further comprising, prior to the step of generating said at least one record of incremental provider observed progress development, the steps of retrieving said evaluation record data; and wherein said step of submitting further comprises submitting said report for a payment from said entity for the skilled-service rendered.

8. The process of claim 7 wherein said step of generating a plan further comprises entering said plan into an input field of a plan record display for storage as plan record data at said host location; and further comprising the steps of:
retrieving said plan record data; and
after said steps of retrieving said evaluation record data and said plan record data, the step of printing a hardcopy of said plan and said evaluation for use at said treatment location.

9. The process of claim 1 wherein:
said step of generating further comprises the steps of generating a plurality of said records of incremental provider observed progress development, each said record associated with one of a plurality of physical therapy treatment goals identified for the patient, and creating a composite record comprising each said record of incremental provider observed progress development along with a record of skilled intervention action used; and
said step of submitting further comprises transmitting said report as electronic data over a data transfer pathway to said entity for a payment.

10. The process of claim 9 wherein said data transfer pathway comprises a network; and further comprising, prior to the step of receiving an input, the step of entering each of said plurality of said records of incremental provider observed progress development made and a date of said treatment session into respective input fields of a treatment record display.

11. The process of claim 1 wherein said physical therapy treatment goal, having been identified from a list, is further modified based upon an evaluation of the patient's condition.

12. A system for tracking skilled-service rendered to a patient at a physical therapy treatment location by a physical therapy provider trained in a physical therapy discipline, comprising:

a composite record, generated at the physical therapy treatment location, comprising at least one record of incremental provider observed progress development, said record of incremental provider observed progress development comprising an indication of incremental patient advances made toward a composite physical therapy treatment goal as compared to a preferred result;

a storage medium at a host location for storing treatment record data comprising at least one of said record of incremental provider observed progress development so generated; and a host processor for automatically generating, using said treatment record data, a patient report for an entity selected from the group consisting of a health care facility, a health care provider, an insurer, the patient, an entity authorized to receive records of the patient, and a record-keeping entity for the provider, wherein said composite physical therapy treatment goal is dynamically modified to create at least one edited treatment goal identified for the patient based upon a development evaluation of said patient during at least one treatment modality.

13. The system of claim 12 wherein said at least one record of incremental provider observed progress development further comprises a description of said goal having been identified based upon an evaluation of the patient's condition and a date of a treatment session; and further comprising an interface for entering said incremental provider observed progress development made and said date into respective input fields of a treatment record display.

14. The system of claim 12 further comprising a user interface for entering, at said host location from a hardcopy of said composite record generated at the physical therapy treatment location, said at least one record of incremental provider observed progress development made into an input field of a treatment record display.

15. The system of claim 12 wherein said composite record further comprises a plan comprising a prescription for follow-up with the patient; and further comprising an interface for entering said plan into an input field of a plan record display for storage at said host location as plan record data.

16. The system of claim 15 wherein: said composite physical therapy treatment goal was identified based upon an evaluation of the patient's condition; said interface further allows for entering a description of said evaluation into an input field of an evaluation record display for storage at said host location as evaluation record data; and said patient report comprises information from said at least one record of incremental provider observed progress development, said plan record data, and said evaluation record data.

17. The system of claim 12 wherein said composite record further comprises a plurality of said records of incremental provider observed progress development, each said record associated with one of a plurality of treatment goals identified based upon an evaluation of the patient's condition; and further comprising a data transfer pathway in communication with said host processor for transmitting said report as electronic data to said entity.

18. The system of claim 17 further comprising a user interface for entering said composite record at the treatment location, said user interface in communication with a second data transfer pathway for transmitting said composite record entered to said host location storage medium.

19. A computer executable program code on a computer readable storage medium for tracking skilled-service rendered to a patient at a physical therapy treatment location by a physical therapy provider trained in a physical therapy discipline, the program code comprising:
a first program sub-code for receiving an input of data comprising at least one record of incremental provider observed progress development, said record of incremental provider observed progress development comprising an indication of incremental patient advances made toward a composite physical therapy treatment goal as compared to a preferred result;
a second program sub-code for storing at least one of said record of incremental provider observed progress development so received, as treatment record data at a host location;
a third program sub-code for generating a patient report using said treatment record data and a host processor, said patient report comprising information from said at least one record of progress for submitting to an entity selected from the group consisting of a health care facility, a health care provider, an insurer, the patient, an entity authorized to receive records of the patient, and a record-keeping entity for the provider; and
a fourth program sub-code for dynamically modifying said composite physical therapy treatment goal to create at least one edited treatment goal identified for the patient based upon a development evaluation of said patient during at least one treatment modality.

20. The program code of claim 19 wherein said input comprising said at least one record of incremental provider observed progress development is first entered through a user interface at said treatment location and temporarily stored as local treatment record data, and said first program sub-code farther comprises instructions for accepting said local treatment record data at said host location; and farther comprising a fourth program sub-code for transmitting said patient report over a data transfer pathway for payment from said entity.

21. The process of claim 1 and farther comprising the step of valuating a quantifiable record of incremental provider observed progress development made toward said composite physical therapy treatment goal as compared to a preferred result.

22. The system of claim 12 wherein said composite record comprises a valuation of a quantifiable record of incremental provider observed progress development.

23. The program code of claim 19 wherein said input of data comprises a valuation of a quantifiable record of incremental provider observed progress development.

* * * * *